United States Patent [19]

Burrington et al.

[11] Patent Number: 4,500,468

[45] Date of Patent: Feb. 19, 1985

[54] CATALYTIC DIMERIZATION OF ACRYLONITRILE

[75] Inventors: James D. Burrington, Richmond Hts.; Marc W. Blachman, Lyndhyrst, both of Ohio

[73] Assignee: The Standard Oil Company, Cleveland, Ohio

[21] Appl. No.: 554,088

[22] Filed: Nov. 21, 1983

[51] Int. Cl.³ .................. C07C 121/30; C07C 120/00
[52] U.S. Cl. ............................................. 260/465.8 D
[58] Field of Search ................................ 260/465.8 D

[56] References Cited

U.S. PATENT DOCUMENTS

| | | | |
|---|---|---|---|
| 3,446,836 | 5/1969 | Lambert et al. | 260/465.8 D |
| 3,590,069 | 6/1971 | Nemec et al. | 260/465.8 D |
| 3,652,642 | 3/1972 | Baba | 260/465.8 D |
| 3,732,281 | 5/1973 | Feldman et al. | 260/465.8 D |
| 3,733,351 | 5/1973 | Watanabe et al. | 260/465.8 D |

*Primary Examiner*—Joseph Paul Brust
*Attorney, Agent, or Firm*—Charles S. Lynch; John E. Miller, Jr.; Larry W. Evans

[57] ABSTRACT

Disclosed is the dimerization of acrylonitrile to α-methyleneglutaronitrile using certain metal aryl sulfinate and selenate catalysts.

23 Claims, No Drawings

CATALYTIC DIMERIZATION OF ACRYLONITRILE

This invention relates to the dimerization of acrylonitrile to α-methyleneglutaronitrile, and to a novel catalyst system therefor. Specifically, the invention relates to the use of certain Group IA or IIA aryl sulfinates and selenates as catalysts for this reaction.

A need exists for an inexpensive source of adiponitrile for making nylon 6,6 by polycondensation with hexamethylene diamine. In addition, adiponitrile can be converted to hexamethylene diamine by known technology. Adiponitrile can be made from α-methyleneglutaronitrile by isomerizing it to 1,4-dicyano-1-butene in high yields and then hydrogenating it to adiponitrile, all by known technology.

It is thus an object of the present invention to provide a new process for catalytically converting acrylonitrile to α-methyleneglutaronitrile.

It is a further object to provide such a process using an inexpensive catalyst system.

Other objects, as well as advantages and embodiments, of the invention will become apparent from a study of this specification, including the claims.

The objects of the present invention are realized according to the present inventive process for making α-methyleneglutaronitrile (α-MGN) which comprises dimerizing acrylonitrile (AN) in the liquid phase in the presence of a metal aryl sulfinate or selenate catalyst having the formula

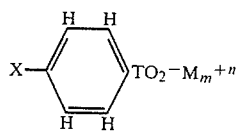

where M is an alkali metal or an alkaline earth metal, T is S or Se, n is 1 or 2, m is 0.5 or 1, n×m=1, and X is selected from H—, nitro, methyl, methoxy and halo, and preferably in the presence of an organic hindered H-donor compound containing at least one —OH group and usually in the presence of a solvent for acrylonitrile that also at least partially dissolves the catalyst.

X is preferably nitro, chloro, methyl or H—.

We have discovered that the hydrogen donor is essential to increase the selectivity of the sulfinate catalyst toward the dimer and minimize conversion of acrylonitrile to higher polymers. Nevertheless, the new catalyst for the dimerization reaction is effective to make the dimer even without the proton donor.

We have further discovered that a solvent is required in order best to effect the desired conversion, and that polar solvents are preferable to non-polar solvents, because polar solvents for a given catalyst increase the percent yield of the dimer based on the amount of acrylonitrile charged to the reactor. Any solvent, but particularly polar solvents, non-reactive under the reaction conditions herein, are suitable provided that they dissolve the acrylonitrile and at least partially dissolve the catalyst.

Solvents applicable include dimethyl sulfoxide (DMSO), benzene, toluene, p-xylene and 1,2,3-trimethylbenzene, the DMSO being of course preferred. However, in the case of the non-polar hydrocarbon solvent a small portion of a solubilizing agent such as a crown ether is usually used to increase the solubility of the catalyst in the reaction mixture. It is also within the scope of the invention to employ the H donor alcohol as the solvent, usually using a volume thereof at least 4 times the acrylonitrile volume.

The sodium benzene sulfinate catalyst is easily available in commerce. In the examples herein, the sodium p-nitro-, p-methyl- and p-chlorobenzene sulfinates were prepared by the procedure of Lindberg via the reduction of the corresponding sulfonyl chloride with sodium sulfite followed by isolation of the sulfite followed by isolation of the sulfinic acid and regeneration of the salt.*

*See B. Lindberg, Acta, Chem. Scand., 17, 377 (1963), and R. N. Haszeldine, J. M. Kidd, J. Chem. Soc., 2901 (1955), both incorporated herein by reference.

Thus, in a typical procedure, p-chlorobenzene sulfonyl chloride (24 g, 0.115 mol) was added to 250 ml $H_2O$ and the resulting suspension was cooled to 0° C. and stirred for 1 hour. Sodium sulfite (15.1 g, 0.120 mol) was then added and the reaction kept at 0° C., and a pH of 7.5 was maintained by addition of 15 percent NaOH using a pH-stat. After two hours the reaction was allowed to warm to 25° C. and stirred for an additional five hours. The resulting clear solution was filtered, the filtrate cooled to 0° C. and 12N HCl at 0° C. was added to the filtrate. The resulting precipitate was collected by filtration and dried under vacuum, to give p-chlorobenzenesulfinic acid as a white solid, 17.3 g (85 percent) mp 94°–96° C. (lit 93°–96° C.). The salt was generated by slurrying the acid in an EtOH/NaOH solution containing an excess of base. The sodium salt was purified by recrystallization from EtOH. Other metal sulfinate catalysts useful according to the present invention are similarly prepared.

In the catalytic process of our invention, the usual temperatures are 50° to 200° C., more usually 65° to 180° C., although higher or lower temperatures can be used in a given case. The optimum temperature in a given reaction depends on the particular recipe, and can be easily determined by routine trial and error testing.

An especially useful combination of catalyst and hydrogen donor in the dimerization reaction of the present invention is where X is methyl, especially sodium p-methylbenzene sulfinate, with the hydrogen donor 2,6-ditertiarybutylphenol.

The following examples are merely illustrative and are not to be considered as limiting.

EXAMPLE 1

Into a 25 mL round bottomed flask equipped with a reflux condenser and a magnetic stirrer were introduced 10 mL dimethyl sulfoxide solvent, 0.03 mol acrylonitrile, 0.0015 mol sodium benzene sulfinate catalyst, and 4 mL tertiary butyl alcohol. In addition 1,2,4,5 tetramethylbenzene was added as an internal standard. The mixture was reacted at 80° C. with stirring under total reflux for 8 hours. The acrylonitrile conversion was 43.2 percent, with a 24 percent yield of α-methyleneglutaronitrile (55.5 percent selectivity) and 19.2 percent yield of higher polymers.

Products from this example and all other runs or examples herein were analyzed on a Varian 3700 gas chromatograph using a 6'×⅛" stainless steel carbowax 20M on chromosorb WAW (80/100) column. The temperature program used was 90° for 2 min. to 190° by 30°/min.

EXAMPLE 2

Example 1 was repeated except that the tertbutyl alcohol was omitted. The results are shown in Table 1.

EXAMPLE 3

Into a 25 mL round bottomed flask equipped with a reflux condenser and a magnetic stirrer were introduced 10 mL dimethyl sulfoxide solvent, 0.03 mol acrylonitrile, and 0.0015 mol sodium benzene selenate catalyst. In addition 1,2,4,5 tetramethylbenzene was added as an internal standard. The mixture was reacted at 80° C. with stirring under total reflux for 8 hours. The acrylonitrile conversion was 10.2 percent, with a 10.2 percent yield of α-methyleneglutaronitrile (100 percent selectivity) and of course, no higher polymers.

EXAMPLES 4–9

Examples 4–9 were effected in the equipment and the manner as in Example 1. The examples are summarized in Table I, together with Examples 1 and 2.

Note that in each comparative instance the H donor reduces activity but increases selectivity to α-methyleneglutaronitrile. Note also that the X group influences acrylonitrile conversion and α-methyleneglutaronitrile to varying degrees.

EXAMPLES 10–13

Examples 10–13 were effected in the equipment and the manner as in Example 1. These examples are summarized in Table II, together with Examples 1, 6 and 7.

EXAMPLES 14–17

Examples 14–17 were effected in the equipment and the manner as in Example 1 except that the temperatures are different when refluxing in the presence of the various solvents. These examples are summarized in Table 3, together with Example 6. It will be noted that the non-polar solvents give lower conversions to α-methyleneglutaronitrile than does DMSO even when conversions of acrylonitrile are considerably higher.

TABLE 1[a]

| | AN Dimerization By pXC$_6$H$_4$SO$_2$Na$^+$ Catalysts | | | | | | |
|---|---|---|---|---|---|---|---|
| Example No. | X | H-Donor | AN Conv. | Yield α MGN[b] | Yield DCB[c] | Sel. to αMGN | Yield Polymer |
| 9921-4 | —CH$_3$ | — | 91.7 | 7.8 | — | 8.5 | 83.9 |
| -5 | —CH$_3$ | tBuOH | 63.9 | 39.6 | — | 62.0 | 24.3 |
| -2 | —H | — | 86.9 | 32.2 | — | 37.0 | 54.6 |
| -1 | —H | tBuOH | 43.2 | 24.0 | — | 55.5 | 19.2 |
| -6 | —Cl | — | 20.2 | 12.2 | — | 60.1 | 8.1 |
| -7 | —Cl | tBuOH | 7.2(10.9) | 11.4(10.9) | — | (100) | — |
| -8 | —No$_2$ | — | 10.0 | 3.4 | — | 34.0 | 6.5 |
| -9 | —No$_2$ | tBuOH | 1.7(4.3) | 4.4(4.3) | trace | (100) | — |

[a]Conditions: 80° C.; 2.0 ml (0.030 mol) AN; 10.0 ml DMSO; 0.0015 mol pXC$_6$H$_4$SO$_2$Na$^+$; 4.0 ml (0.05 mol) alcohol (tBuOH), when present; reaction time 8 hours; numbers in ( ) normalized to 100% material balance.
[b]α-methyleneglutaronitrile
[c]1,4-dicyanobutenes TABLE 2[a]

| | AN Dimerization by pXC$_6$H$_4$SO$_2$Na$^+$ Catalysts - Effect of Proton Donor | | | | | | |
|---|---|---|---|---|---|---|---|
| Example No. | X | H-Donor | AN Conv. | Yield α MGN[b] | Yield DCB[c] | Sel. to αMGN | Yield Polymer |
| −7 | —Cl | tBuOH | 7.2(10.9) | 11.4(10.9) | — | (100) | — |
| −10 | —Cl | iPrOH | 23.9 | 11.0 | — | 46.0 | — |
| −11 | —Cl | EtOH | 54.7 | 8.4 | — | 15.3 | — |
| −12 | —Cl | MeOH | 87.6 | 9,8 | — | 11.2 | — |
| 6 | —H | — | 20.3 | 12.2 | — | 60.1 | 8.1 |
| 1 | —H | tBuOH | 43.2 | 24.0 | — | 55.5 | 19.2 |
| 13 | —H | DTP[d] | 15.0(19.0) | 20.0(19.0) | — | (100) | — |

[a]Same conditions as Table I with substitutions being mole for mole.
[b]α-methyleneglutaronitrile
[c]1,4-dicyanobutenes
[d]2,6-ditertbutylphenol
figures in parentheses are normalized TABLE 3[a]

| | AN Dimerization by pClC$_6$H$_4$SO$_2$Na$^+$ in Aromatic Solvents[a] | | | | | | |
|---|---|---|---|---|---|---|---|
| Example No. | x | H-Donor | AN Conv. | Yield α MGN[b] | Yield DCB[c] | Sel. to αMGN | Yield Polymer |
| 6 | DMSO (No Crown) | 80° C. | 20.3 | 12.2 | — | 60.1 | 8.1 |
| 14 | Benzene | 80° C. | 5 | 1.2 | — | 24 | 4 |
| 15 | Toluene | 110° C. | 10 | 0.6 | — | 6 | 9 |
| 16 | p-Xylene | 138° C. | 40 | 2.4 | — | 6 | 37 |
| 17 | 1,2,3-trimethylbenzene | 175° C. | 30 | 5.0 | — | 17 | 25 |

[a]Same conditions as Table I, at reaction temperatures indicated; 0.35 ml (0.0016 mol) 15-Crown-5; no alcohol used.
[b]α-methyleneglutaronitrile
[c]1,4-dicyanobutenes As will be evident to those skilled in the art various modifications of this invention can be made or followed in the light of the foregoing disclosure and discussion without departing from the spirit and scope of the disclosure of from the scope of the claims.

We claim:

1. A process for making α-methyleneglutaronitrile which comprises dimerizing acrylonitrile in the presence of a catalytic amount of a sulfinate or selenate catalyst having the formula

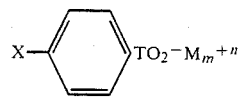

where M is an alkali metal or an alkaline earth metal, T is S or Se, n is 1 or 2, m is 0.5 or 1, n×m=1, and X is selected from H—, nitro, methyl, methoxy and halo.

2. A process of claim 1 wherein X is H.
3. A process of claim 1 where T is S.
4. A process of claim 3 wherein X is nitro.
5. A process of claim 3 wherein X is methoxy.
6. A process of claim 3 wherein X is halo.
7. A process of claim 6 wherein halo is chloro.
8. A process of claim 6 wherein halo is iodo.
9. A process of claim 6 wherein halo is bromo.
10. A process of claim 6 wherein halo is fluoro.
11. A process of claim 3 wherein X is methyl.
12. A process for making α-methyleneglutaronitrile which comprises dimerizing acrylonitrile in the liquid phase in the presence of a catalytic amount of a metal aryl sulfinate catalyst having the formula

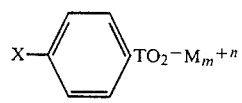

where M is an alkali metal or an alkaline earth metal, T is S, n is 1 or 2, m is 0.5 or 1, n×m=1, and X is selected from H—, nitro, methyl, methoxy and halo.

13. A process for making α-methyleneglutaronitrile which comprises dimerizing acrylonitrile in the presence of a catalytic amount of a catalyst having the formula

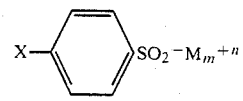

where M is an alkali metal or an alkaline earth metal, n is 1 or 2, m is 0.5 or 1, n×m=1, and X is selected from H—, nitro, methyl, methoxy and halo, in the presence of an organic hindered H-donor compound containing at least one —OH group.

14. A process of claim 13 wherein X is methyl and the hydrogen donor is 2,6-diteritiarylbutylphenol.

15. A process of claim 13 wherein X is methyl and M is sodium.

16. A process for making α-methyleneglutaronitrile which comprises dimerizing acrylonitrile in the presence of a catalytic amount of a metal aryl sulfinate catalyst having the formula

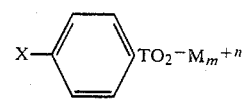

where M is an alkali metal or an alkaline earth metal, T is S, n is 1 or 2, m is 0.5 or 1, n×m=1, and x is selected from H—, nitro, methyl, methoxy and halo, having an atomic weight over 35, in the presence of an organic hindered H-donor compound containing at least one —OH group and in the presence of a solvent for acrylonitrile that also at least partially dissolves the catalyst.

17. A process for making α-methyleneglutaronitrile which comprises dimerizing acrylonitrile in the presence of a catalytic amount of a catalyst having the formula

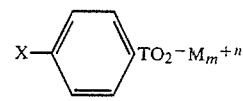

where M is an alkali metal or an alkaline earth metal, T is S or Se, n is 1 or 2, m is 0.5 or 1, n×m=1, and X is selected from H—, nitro, methyl, methoxy and halo, in the presence of an organic hindered H-donor compound containing at least one —OH group and in the presence of a polar solvent for acrylonitrile that also at least partially dissolves the catalyst.

18. A process of claim 17 where X is methyl.
19. A process of claim 17 where X is H.
20. A process of claim 17 where X is nitro.
21. A process of claim 17 where X is methoxy.
22. A process of claim 17 where X is halo.
23. A process of claim 22 where halo is chloro.

* * * * *